US010121820B1

(12) United States Patent
Chen et al.

(10) Patent No.: US 10,121,820 B1
(45) Date of Patent: Nov. 6, 2018

(54) PROTECTIVE CAPS FOR SMALL IMAGE SENSOR MASKING AND MOUNTING PROCESS

(71) Applicant: OmniVision Technologies, Inc., Santa Clara, CA (US)

(72) Inventors: Teng-Sheng Chen, Hsinchu (TW); Yuan-Wen Cheng, Hsinchu (TW); Chia-Yang Chang, Sunnyvale, CA (US); Yi Qin, Shanghai (CN); Wen-Jian Xia, Shanghai (CN)

(73) Assignee: OmniVision Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/655,494

(22) Filed: Jul. 20, 2017

(51) Int. Cl.
*A61B 1/00* (2006.01)
*H01L 27/146* (2006.01)
*A61B 1/04* (2006.01)

(52) U.S. Cl.
CPC ...... *H01L 27/14685* (2013.01); *A61B 1/0011* (2013.01); *A61B 1/00163* (2013.01); *A61B 1/04* (2013.01); *H01L 27/1469* (2013.01); *H01L 27/14618* (2013.01); *H01L 27/14623* (2013.01); *H01L 27/14627* (2013.01); *H01L 27/14634* (2013.01); *H01L 27/14636* (2013.01); *H01L 27/14645* (2013.01)

(58) Field of Classification Search
CPC ............... H01L 27/14627; A61B 1/00163
See application file for complete search history.

(56) References Cited

U.S. PATENT DOCUMENTS

2010/0085473 A1* 4/2010 Shiung ............... G03B 19/00
348/373
2017/0108692 A1* 4/2017 Kitano ............ G02B 23/2469

* cited by examiner

Primary Examiner — William Harriston

(57) ABSTRACT

A method of processing an image sensor system, comprising steps of placing a first cover member on top of an image sensor; coating the image sensor and the first cover member with a dark coating agent; removing the first cover member from the image sensor; placing a second cover member on top of the image sensor; affixing the image sensor on to a permanent mount to form an electrical coupling between the image sensor and the permanent mount; removing the second cover member from the image sensor; wherein the first cover member completely covers a top portion of the image sensor; and wherein the second cover member includes an internal rib configured to form a contact seal with the image sensor.

18 Claims, 20 Drawing Sheets

PROTECTIVE CAPS FOR SMALL IMAGE SENSOR MASKING AND MOUNTING PROCESS

TECHNICAL FIELD

This disclosure relates generally to a small image sensor's packaging processes, such as masking, coating, and mounting. In particular, a small image sensor is an image sensor that has a width of about one millimeter or less. Conventional masking, coating, and mounting processes that are used to incorporate an image sensor into its applicable system are replaced by the processes described in the present disclosure.

BACKGROUND INFORMATION

Image sensing devices use opto-electric technology to acquire images. Image sensors that employ Charge Coupled Device (CCD) or Complementary Metal Oxide Semiconductor (CMOS) designs are examples of this device category. Image sensors have been widely used in mobile phones, tablet and laptop computers, automobile cameras, surveillance cameras, endoscope systems, etc. For small image sensor applications, such as medical endoscopes or catheter-based endoscopes, the image sensors are increasingly made smaller. Recent versions of medical endoscope image sensors are approaching a width that is approximately one millimeter, e.g., 1.05×1.05 mm or even less. With such a small sensor, conventional image sensor packaging process that is suitable for larger sensors may no longer be suitable.

BRIEF DESCRIPTION OF THE DRAWINGS

Non-limiting and non-exhaustive examples of the invention are described with reference to the following figures, wherein like reference numerals refer to like parts throughout the various views unless otherwise specified.

Figure 1A:
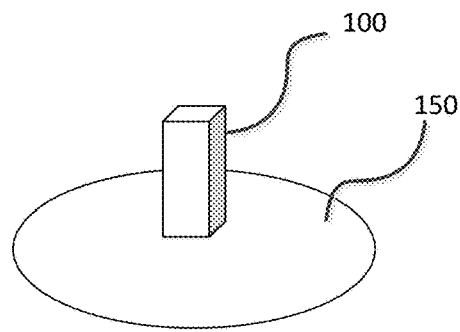
FIGS. 1A through 1F show an exemplary process to coat an image sensor with a dark coating agent.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

In the following description, numerous specific details are set forth to provide a thorough understanding of the examples. One skilled in the relevant art will recognize; however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "example" or "embodiment" means that a particular feature, structure, or characteristic described in connection with the example is included in at least one example of the present invention. Thus, the appearances of "example" or "embodiment" in various places throughout this specification are not necessarily all referring to the same example. Furthermore, the particular features, structures, or characteristics may be combined in any suitable manner in one or more examples.

Throughout this specification, several terms of art are used. These terms are to take on their ordinary meaning in the art from which they come, unless specifically defined herein or the context of their use would clearly suggest otherwise.

Figure 7A:
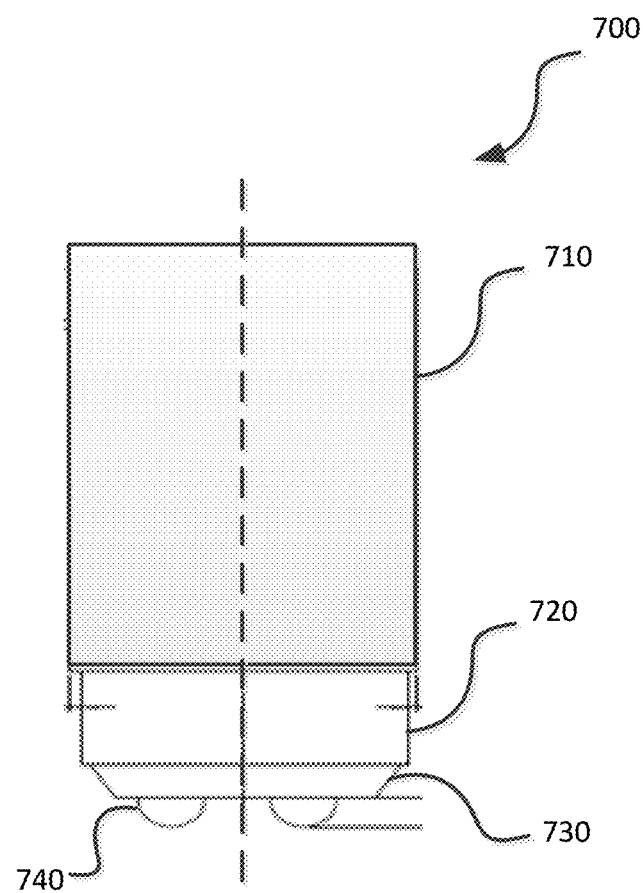
FIGS. 7A and 7B show cross sectional side views an exemplary small image sensor.

FIG. 7A shows a cross sectional side view of an exemplary small image sensor 700. This image sensor is called a small image sensor partly due to the fact that its width approaches one millimeter, e.g., 1.05×1.05 mm, or even less. The small sensor 700 has applications in areas that include medical endoscopy, small area visual inspection, etc. For example, the small sensor 700 may be integrated into an endoscope that can fit into a small cavity for visual inspection and image acquisition.

As shown in FIG. 7A, the small image sensor 700 includes a lens system 710, a cover glass 720, a silicon related structure 730, and solder balls 740. The cover glass 720, the silicon structure 730, and the solder balls 740 may be CSP (Chip Scale Package) components, meaning that these components are first assembled together into a chip scale package, which is then singulated (e.g., diced or cut) into individual units. The lens barrel 710 may be installed onto each individual CSP unit to form the small image sensor 700.

The silicon structure 730 includes the key components (not shown in the drawing) of an image sensor such as a CMOS based image sensor. These key components may include photodiodes, various transistor gates (transfer gate, source follower gate, reset gate, row select gate, etc.), doped regions in a silicon substrate (such as a floating diffusion node and a pinning layer), color filters, microlenses, various metal connects, and so on.

The widths of the lens system 710, the cover glass 720, and the silicon structure 730 may be similar to each other, and contribute to the overall width of the small sensor 700, which may be about 1×1 mm or less, e.g., 1.05×1.05 mm or less. Exemplary heights of the lens system 710, the cover glass 720, and the silicon structure 730 are 1.636 mm, 0.4 mm, and 0.13 mm, respectively. When the small sensor is affixed to a permanent mount, the solder balls 740 establish mechanical and electrical connection between the silicon structure 730 and any underlying permanent mount. Each solder ball 740 has an exemplary hemispherical shape. Exemplary height and width (i.e., diameter) of the solder ball 740 are 0.12 mm and 0.2 mm, respectively.

Figure 7B:
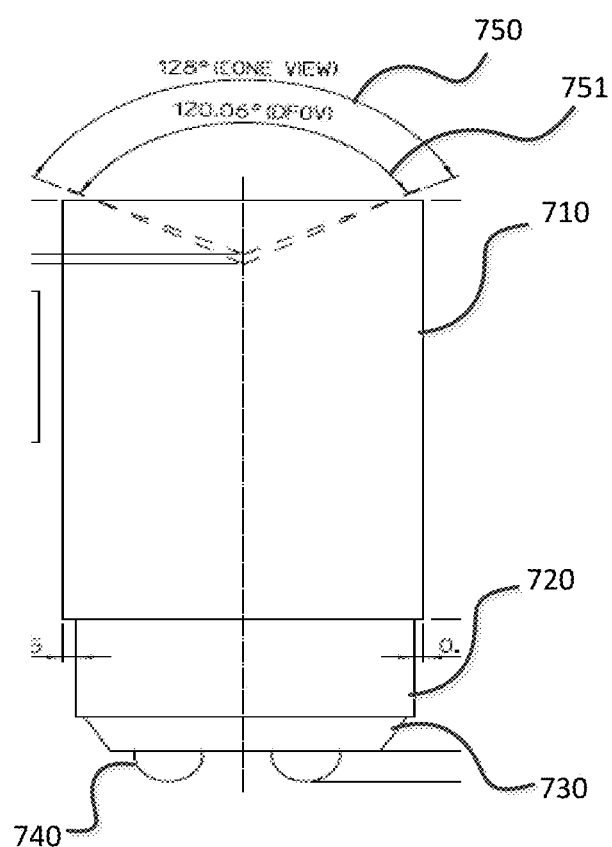

The lens system 710 may be a lens barrel, a lens stack, or an assembly that includes multiple lenses. A key property of the lens system 710 is its field of view (FOV), which may be represented by a solid angle. The lens system 710 has an exemplary FOV of about 120 degrees solid angle. FIG. 7B shows the same small sensor 700 as in FIG. 7A, and additionally includes a mechanical cone view stop 750 of 128 degrees, and an optical DFOV requirement 751 with a smaller value of 120.06 degrees, which is the actual FOV angle.

The lens system 710 may be coated with a dark coating material, such as a black coat or paint, for light shielding purposes. Without this dark coating material, light entering the lens system 710 may exit the side of the long lens, instead of entering the silicon structure 730 below to impact the light sensing components within it.

Figure 8A:
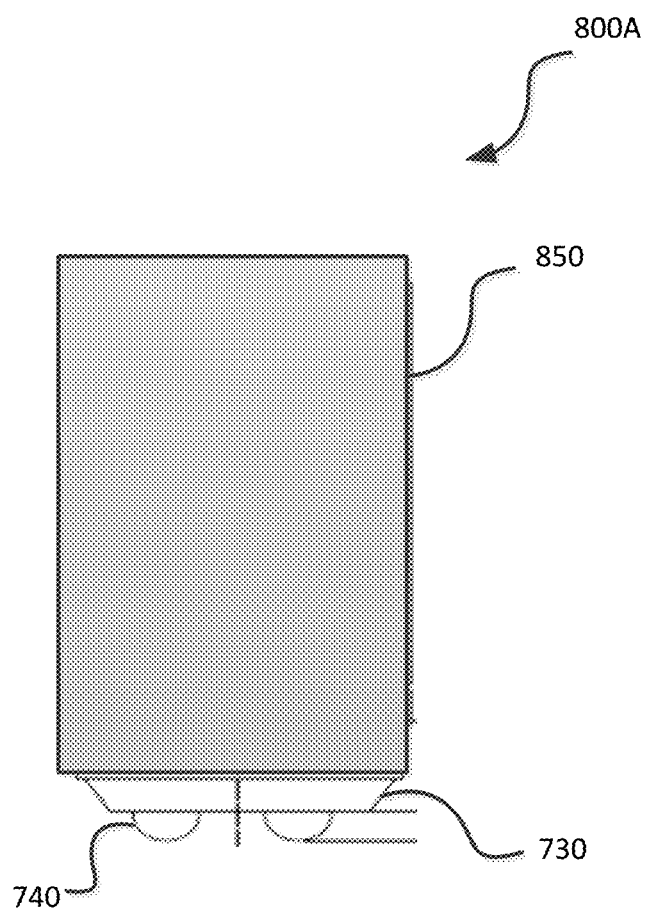
FIGS. 8A and 8B are cross sectional side views, showing a small image sensor with complete side wall dark coating, and an exemplary small image sensor with partial side wall dark coating, respectively.

FIG. 8A shows a side view of a dark coated small sensor 800A, which is similar to the (uncoated) small image sensor 700 in FIG. 7A, but with its lens system 710 and the cover glass 720 coated with a black paint to act as a light shield, thereby forming a coated portion 850. The lens system 710 and the cover glass 720 are thus obscured from direct view. Optionally, the silicon structure 730 and the solder balls 740 are left uncoated.

First Exemplary Process to Package a Small Image Sensor

FIGS. 1A through 1F show an exemplary process to apply a dark or black coating agent to the uncoated small sensor 700 as shown in FIG. 7A, in order to achieve the coated small sensor 800A as shown in FIG. 8A.

Figure 1B:
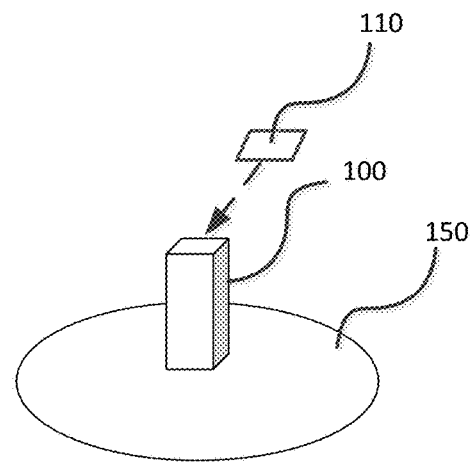
Figure 1C:
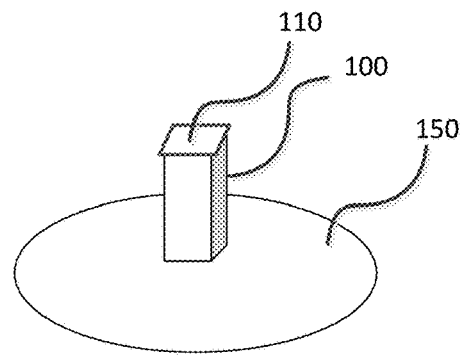

First, as shown in FIG. 1A, a small image sensor 100, as exemplified by the uncoated small sensor 700 in FIG. 7A, is removably attached to a temporary mount 150. This attachment may be achieved by the use of some glue agent. Then, as shown in FIG. 1B, a masking tape 110 is removably attached (indicated by a dashed arrow line) to the top of the small image sensor 100. This attachment is generally performed manually, especially when the small sensor 100 has a width of about one millimeter or less. The masking tape 110 may be a thermal glue tape, wherein the thermal glue is activated by heat to affix the masking tape 110 to the top of the small sensor 100. The result is shown in FIG. 1C, wherein the masking tape 110 is affixed to the small sensor 100, which is in turn affixed to the temporary mount 150. These members 110-100-150 form a tape-sensor-mount assembly for a subsequent coating process.

Figure 1D:
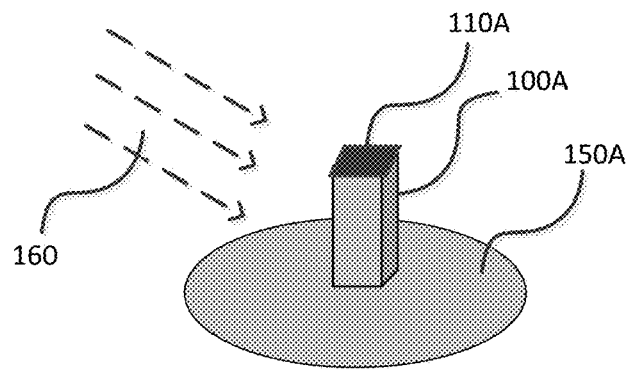

Then, as shown in FIG. 1D, a dark coating agent 160, such as a black coat or paint, is applied to the entire tape-sensor-mount assembly. As a result, the tape 110, the sensor 100, and the mount 150, are now each coated, thereby becoming a coated tape 110A, a coated sensor 100A, and a coated mount 150A.

Figure 1E:
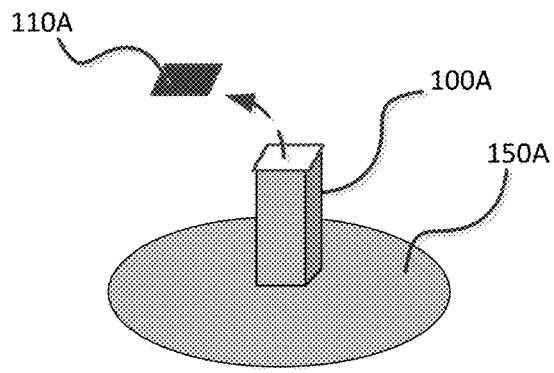
Figure 1F:
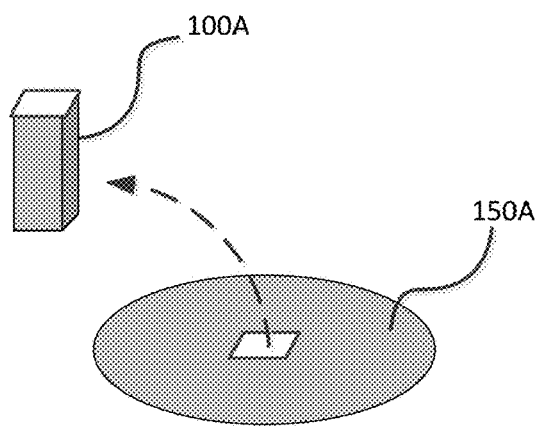

Next, as shown in FIG. 1E, the coated tape 110A is removed from the coated sensor 100A (as indicated by a dashed arrow curve). This removal step, similar to the attachment step shown in FIG. 1B, is also performed manually in general. The result is that the top of the coated sensor 100A is uncoated, because of the masking by the tape 110/110A.

Finally, the coated small sensor 100A is detached from the temporary base 150A, to be further processed in later packaging steps. It should be noted that the process shown in FIGS. 1A through 1F produces a coated image sensor that is exemplified by the coated small sensor 800A, as shown in FIG. 8A.

The above disclosed masking-painting process has several shortcomings. First, the attaching and removing the masking tape 110/110A causes the overall production throughput rate to be low, which leads to low process efficiency. Second, the manual labor involvement increases production cost. Third, the manual process is not suitable for a small sensor that has a width of about one millimeter or less, as explained below.

Figure 10:
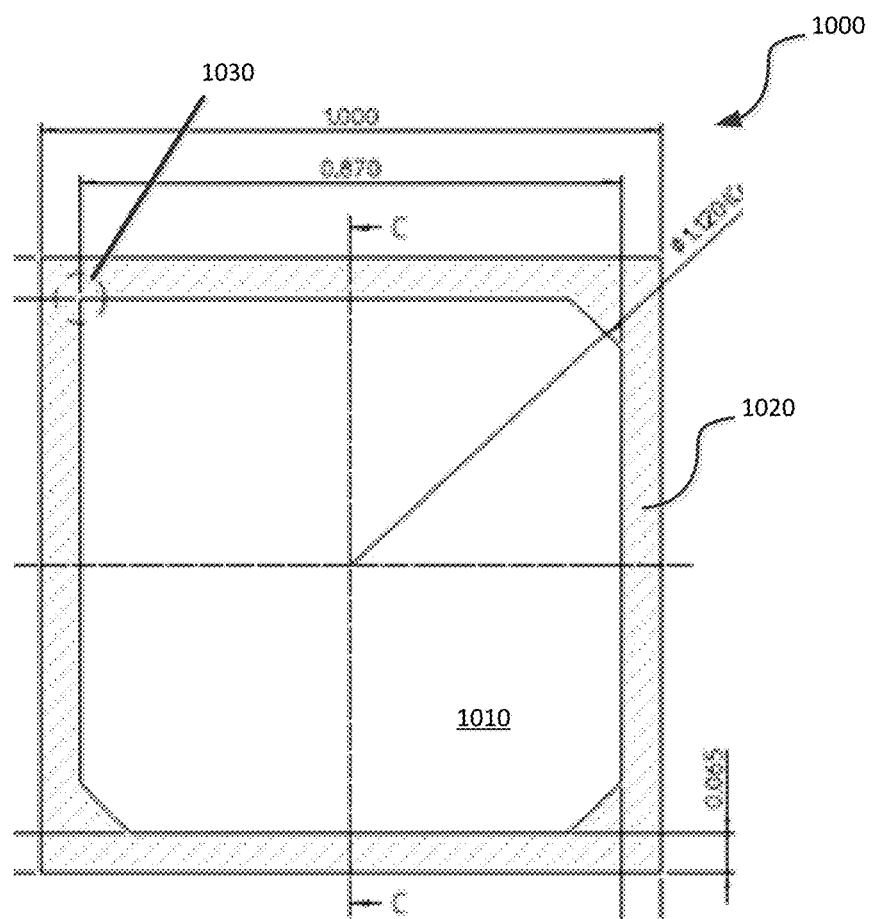
FIG. 10 is a top view of an exemplary small image sensor.

FIG. 10 is a top view of an exemplary small image sensor 1000, which is also exemplified by sensors 100, 100A, 700, and 800A in the disclosure above. This small image sensor 1000 has an exemplary width of one millimeter, meaning a top cross sectional dimension of 1×1 mm, as shown in FIG. 10. The small image sensor 1000 includes, at its center, a sensing area 1010, which comprises image sensing pixels (not individually shown). This central sensing area 1010 has an exemplary square shape, with a width of about 0.870 mm, as shown in FIG. 10. It is appreciated that square-shaped sensing area 1010 has three corners that are blunted, and a fourth corner 1030 that is not bunted. The non-blunted corner 1030 serves as a marker for pin (solder ball) orientation. For example, the corner 1030 marks the orientation of pin (solder ball) number one. The small image sensor 1000 also includes, in its periphery, a peripheral zone 1020, which is a zone (shaded in FIG. 10) around all the sides of the central sensing area 1010, and has an exemplary width of about 0.065 mm.

The manual process of attaching and removing the masking tape 110/110A with regard to the top of a small sensor such as the sensors 100/100A and/or 1000 is difficult, because the width of the peripheral zone 1020 is too small. That is, an exemplary space of only 0.065 mm is not enough for a reasonably accurate manual taping and un-taping process.

Second Exemplary Process to Package a Small Image Sensor

Accordingly, a process involving a protective cap to apply a dark coating agent to a small image sensor is disclosed in herein, along with FIGS. 2A through 2F. The numbering of some parts in FIGS. 2A through 2F is analogous to the parts in FIGS. 1A through 1F. For example, a small image sensor is numbered as 100 in FIGS. 1A-F, and similarly as 200 in FIGS. 2A-F; a temporary mount is numbered as 150 in FIGS. 1A-F, and similarly as 250 in FIGS. 2A-F; and so on.

Figure 2A:
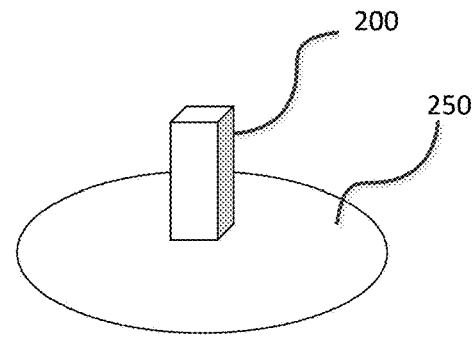
FIGS. 2A through 2F show another exemplary process to coat a small image sensor, with the use of a short protective cap.
Figure 2B:
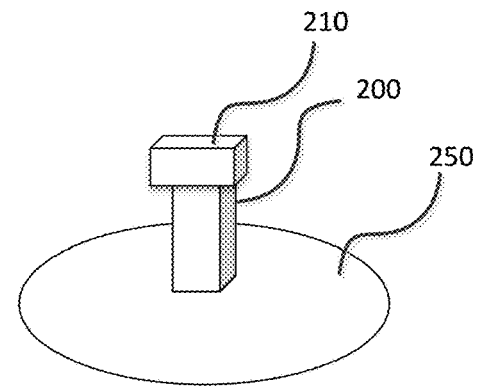

First, as shown in FIG. 2A, a small image sensor 200 (with an exemplary width of about one millimeter or less) is removably attached to a temporary mount 250. This attachment may be achieved by the use of some glue agent (e.g., a heat activated glue agent). Then, a first cover member 210 is removably attached to cover the top portion of the small image sensor 200. The first cover member 210 may be a protective cap, and is exemplarily referred to as a short protective cap 210. The covering is performed by machine automation, but a manual process is also feasible. The weight of the first cover member 210, and/or contact friction contribute to holding it in place to cover the top portion of the small sensor 200. The result is shown in FIG. 2B, wherein the first cover member 210 is affixed to the small sensor 200, which is in turn affixed to the temporary mount 250. These members 210-200-250 form a cover-sensor-mount assembly for a subsequent coating process.

Figure 2C:
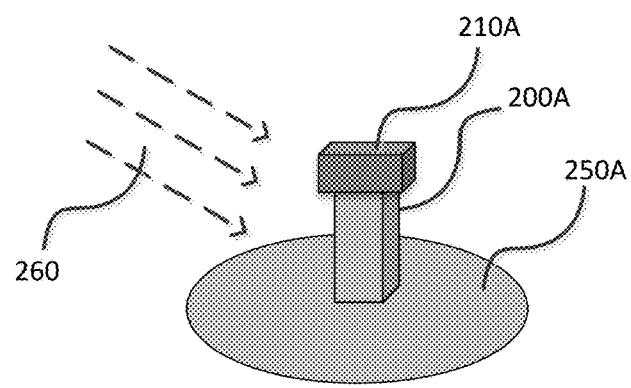

Then, as shown in FIG. 2C, a dark coating agent 260, such as a black coat or paint, is applied to the entire cover-sensor-mount assembly. As a result, the first cover member 210, the sensor 100, and the mount 150, are now each coated, thereby becoming a coated first cover member 210A, a coated sensor 200A, and a coated mount 250A.

Figure 2D:
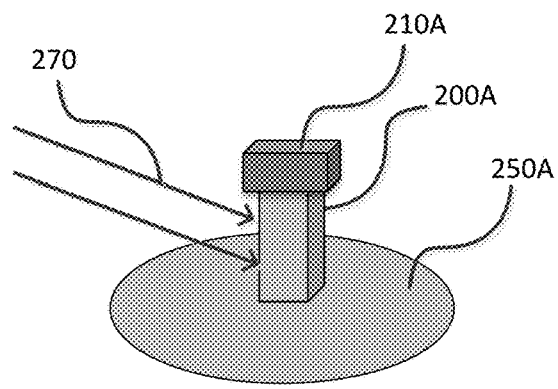

Next, as shown in FIG. 2D, an optional process applies laser 270 to engrave the coated sensor 200A to create marks for medical product tracing, and/or to cut/shape clear edges of the black coating to enhance the appearance of the coated sensor 200A.

Figure 2E:
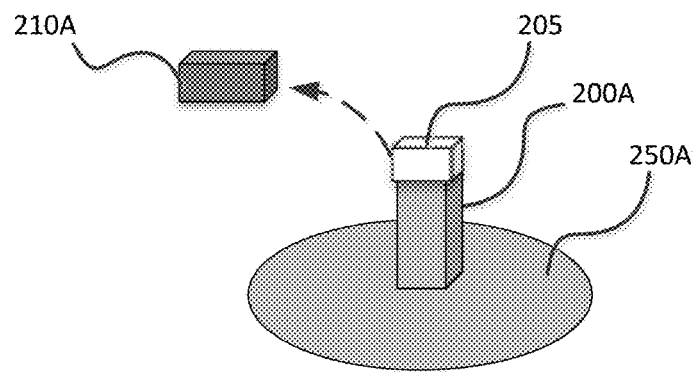
Figure 2F:
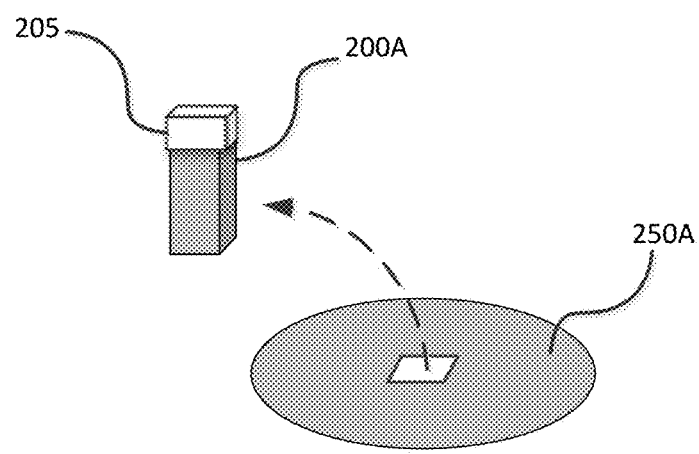

Next, as shown in FIG. 2E, the coated first cover member (short protective cap) 210A is removed from the coated sensor 200A (as indicated by a dashed arrow curve). This removal step may be performed by machine automation, but manual process is also feasible. The result is that the top portion of the coated sensor 200A is shown as uncoated, and is exemplified by an uncoated top portion 205 as part of the coated sensor 200A. Finally, the coated small sensor 200A is detached from the temporary base 250A, to be further processed in later packaging steps.

It should be noted that the process shown in FIGS. 2A through 2F produces a coated image sensor that is different from what is produced by the process shown in FIGS. 1A through 1F. This is explained in the following.

Figure 8B:
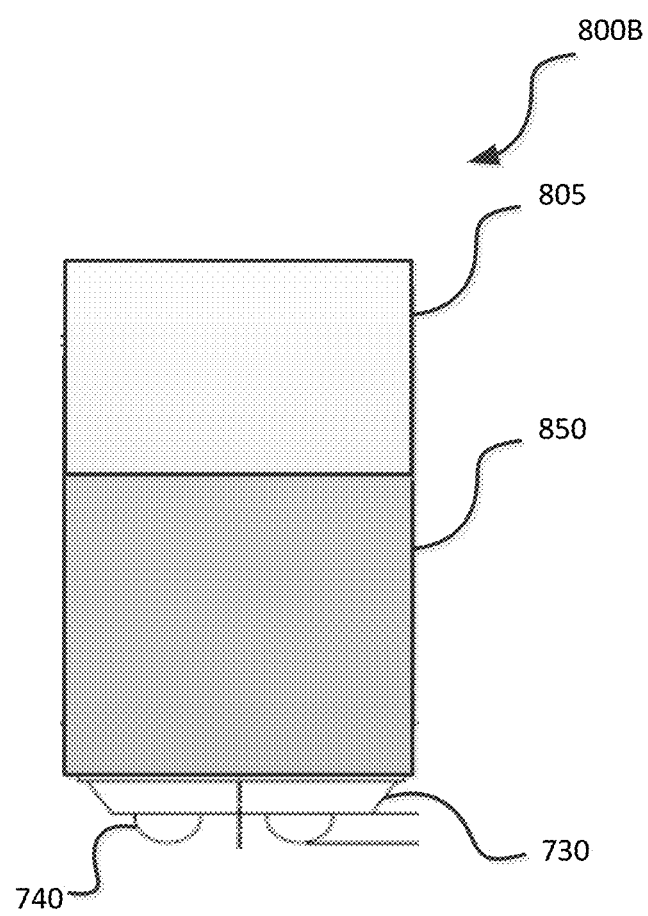

FIG. 8B shows a side view of a partially dark-coated small sensor 800B, which is exemplified as the coated small sensor 200A in FIGS. 2A through 2F. Comparing with the fully coated sensor 800A in FIG. 8A, the small sensor 800B is only partially coated with the black paint, which acts as a light shield, thereby forming a coated portion 850. More specifically, just like the full coated sensor 800A, the partially coated sensor 800B has the black paint to coat its lens 710 and cover glass 720 (not labeled in FIG. 8B), but importantly, a top portion 805 (e.g., the top portion of the lens 710) is left uncoated. Optionally, just like the fully coated sensor 800A, the silicon structure 730 and the solder balls 740 are left uncoated.

In summary, FIG. 8A shows the small sensor 800A whose side (e.g., lens plus cover glass) is fully coated with the black paint. In contrast, FIG. 8B shows the small sensor 800B whose side (e.g., lens plus cover glass) is only partially coated with the black paint, thereby forming the coated portion 850. Crucially, the top portion 805 of the small sensor 800B is left uncoated, because the short protective cap 210/210A in FIGS. 2A through 2F covers this top portion 805, and prevents it from being coated by the dark coating agent 260 as shown in FIG. 2C. In FIG. 8B, the top uncoated portion 805 has an exemplary height of 0.946 mm. The coated portion 850 has an exemplary height of 1.2±0.05 mm (not shown exactly to scale). The silicon related structure 730 and/or the solder balls 740 may optionally be coated with the black paint, and become part of the coated portion 850.

The use of the short protective cap in the second exemplary process (FIGS. 2A through 2F) obviates the need for manual taping/un-taping in the first exemplary process (FIGS. 1A through 1F). This allows a small image sensor (about 1 mm width or less) to be coated with a dark coating agent in a reliable manner. It also produces a specific coating result as shown in FIG. 8B, wherein the top portion 805 of the small sensor 800B is left uncoated. This uncoated portion 805 is beneficial to a subsequent process to mount the small sensor 800B onto a permanent mount as part of a larger sensor system. Details are disclosed further later.

Referring to FIG. 8B, when a small sensor such as sensor 800B is mounted onto a permanent mount as part of a larger sensor system, the solder balls 740 are first partially melted by heating and then solidified by cooling to form a connection with the permanent mount. This heating and cooling process is known as reflow in the art of surface mount technology (SMT). Reflow and other various SMT procedures tend to produce an air that is contaminated with smoke, chemicals, particulates, etc. This contaminated SMT air may reach the top of the sensor 800B to contaminate its lens, e.g., by depositing chemicals and/or particulates on to the lens (situated at top of the sensor 800B) and blocking light path coming into the sensor 800B. Therefore, it is beneficial to protect the top portion of the sensor 800B during SMT processes such as reflow.

Third Exemplary Process to Package a Small Image Sensor

Accordingly, a process involving a second protective cap to protect a coated image sensor from being contaminated during an SMT process is disclosed herein, along with FIGS. 3A through 3F. The numbering of some parts in FIGS. 3A through 3F is analogous to FIGS. 2A through 2F. For example, a coated small image sensor is numbered as 200A in FIGS. 2A-F, and similarly as 300A in FIGS. 3A-F; a temporary mount is numbered as 250 in FIGS. 2A-F, and similarly as 350 in FIGS. 3A-F; a first cover member is numbered as 210 in FIGS. 2A-F whereas a second cover member is numbered as 310 in FIGS. 3A-F; and so on.

Figure 3A:
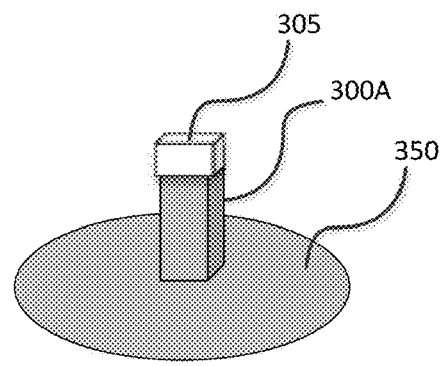
FIGS. 3A through 3F show an exemplary process to mount a coated small image sensor on to a permanent mount, with the use of a long protective cap.

First, as shown in FIG. 3A, a coated small image sensor 300A is removably attached to a temporary mount 350. This attachment may be achieved by the use of some (thermally activated) glue agent. The coated small image sensor 300A is analogous to the coated small image sensor 200A in FIGS. 2A-F, and has an uncoated top portion 305, which is analogous to the uncoated top portion 205 in FIGS. 2A-F.

Figure 3B:
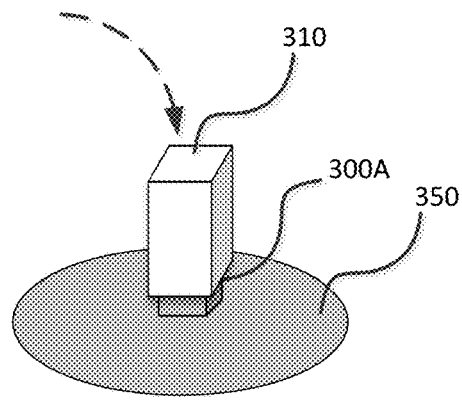

Then, a second cover member 310 is removably attached to cover an upper portion of the small image sensor 300A. The second cover member 310 may be a protective cap, and is exemplarily referred to as a long protective cap 310. The long protective cap 310 is longer than the short protective cap 210 as shown in FIGS. 2A-F. The covering step in FIG. 3B is performed by machine automation, but a manual process is also feasible. The second cover member 310 forms a contact seal with the small image sensor 300A, e.g., a contact seal with the top portion 305 of the sensor 300A. The weight of the second cover member 310, and/or the contact seal friction between the second cover member 310 and the image sensor 300A contribute to holding it in place to cover the top portion 305 of the small sensor 300A. The result is shown in FIG. 3B, wherein the second cover member 310 is affixed to the coated small sensor 300A, which is in turn affixed to the temporary mount 350.

Figure 3C:
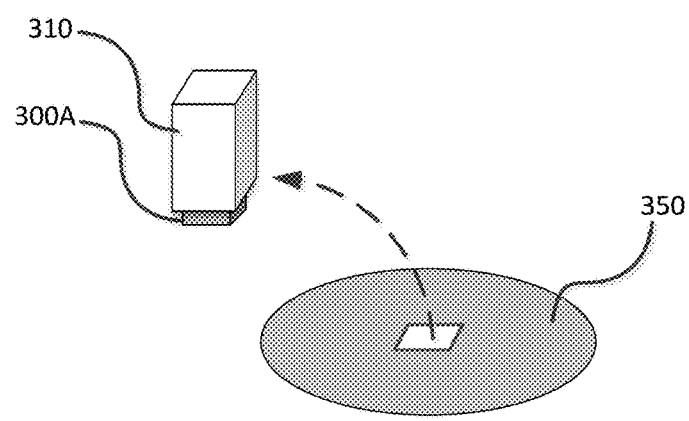

Then, as shown in FIG. 3C, the assembly of the small sensor 300A that is capped with the long protective cap 310 is removed from the temporary mount 350 for subsequent processing, such as SMT mounting onto a permanent mount as part of a larger sensor system. The SMT mounting process is disclosed immediately below.

Figure 3D:
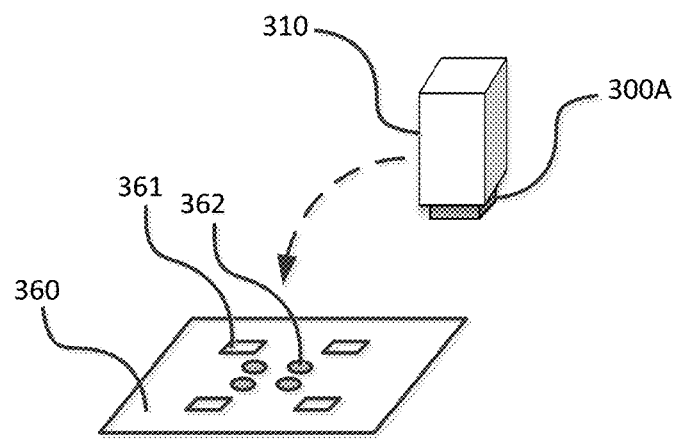

In FIG. 3D, the small sensor 300A that is capped with the long protective cap 310 is placed (as indicated by a dashed arrow curve) onto a permanent mount 360. The permanent mount 360 is a part of a final image sensor package system wherein the sensor 300A is incorporated with other system components to perform image sensing. For example, the final sensor system may be a catheter-based endoscope, and the permanent mount 360 may be incorporated on to the tip of the catheter, which contains metallic connection pads and wiring to relay electric signals from the image sensor 300A to be further processed outside the catheter-based endoscope. Accordingly, the permanent mount 360 includes a number of exemplary solder/flux pads 362, which are to be coupled to solder balls (not labeled) at the bottom of the sensor 300A. Such solder balls are exemplified by the solder balls 730 of the sensor 800B in FIG. 8B. Also included in the permanent mount 360 are a number of optional support pads 361 to support the second cover member 310 when it is placed on the permanent mount 360. The placement of the small sensor 300A that is capped with the long protective cap 310 on to the permanent mount 360 with the solder pads 362 and the support pads 361 is further illustrated in FIG. 4, as disclosed immediately below.

Figure 3E:
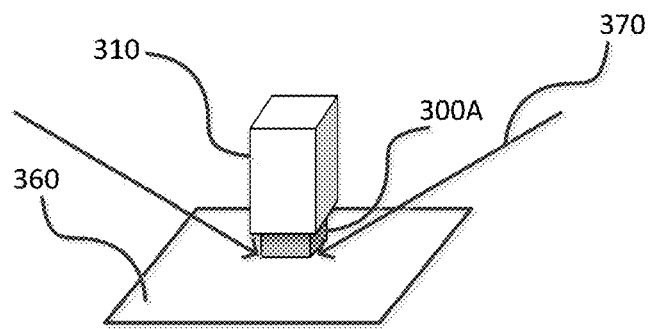
Figure 3F:
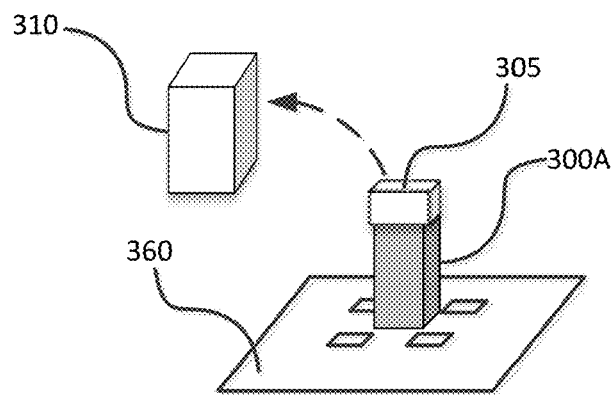
Figure 4:
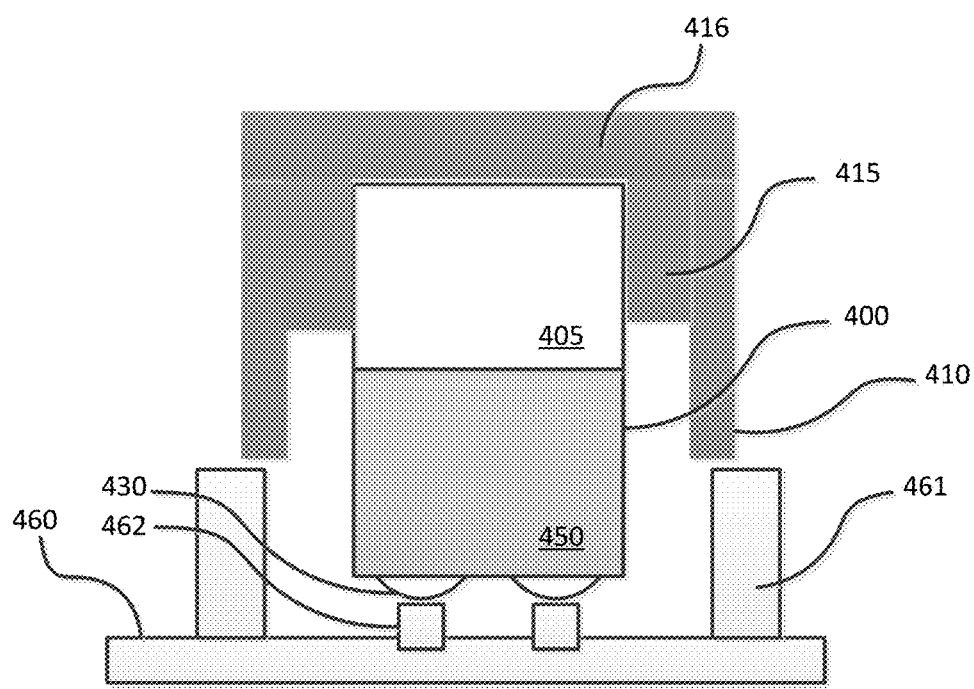
FIG. 4 is a cross sectional side view showing a long protective cap covering a coated small image sensor that is placed on a permanent mount.

FIG. 4 is a cross sectional side view of an image sensor 400 that is capped with a long protective cap 410, wherein both the image sensor 400 and the long protective cap 410 are being placed on to a permanent mount 460 that includes a number of support pads 461, and a number of solder pads 462. The image sensor 400 is also exemplified by the sensor 300A in FIGS. 3A-F, and the sensor 800B in FIG. 8B. The image sensor 400 includes an uncoated top portion 405, and a bottom portion 450 that is coated with a dark coating agent. The sensor 400 includes solder balls 430, which are exemplified by the solder balls 730 as shown in FIG. 8B. The solder balls 430 rest on the solder pads 462 of the permanent mount 460. SMT techniques, e.g., reflow, may be used to couple the solder balls 430 with the solder pads 462, in order to establish an electrical connection, so that image signals may be relayed from the sensor 400 to some outside unit for further processing.

The long protective cap 410 is exemplified by the second cover member 310 in FIGS. 3A-F. The long protective cap 410 includes an internal rib member 415 that forms a contact seal with the sensor 400. In this particular example, the internal rib 415 forms a contact seal only with the uncoated top portion 405 of the sensor 400. The weight of the long protective cap 410, and/or the contact seal between the internal rid 415 and the uncoated portion 405, functions to affix the long protective cap 410 on to the sensor 400. When the sensor 400 that is capped with the long protective cap 410 is placed on to the permanent mount 460, the long protective cap 410 rests on the support pads 461, as shown in FIG. 4.

It is appreciated that the internal ribs 415 are situated to be flush with a top component 416 of the long protective cap 410. This causes the top component 416 to be in contact with the top of the image sensor 400, as shown in FIG. 4. This configuration contributes to the contact stability of the alternative long protective cap 410 on top of the sensor 400. In addition, this design helps to ensure that the solder balls 430 will rest securely on the solder pads 462. Alternatively, the internal ribs 415 may not be situated to be flush with the top component 416, wherein the top component 416 may not be in contact with the top of the image sensor 400 (not shown in FIG. 4).

In the present embodiment, the long protective cap 410 has exemplary widths of about 2.6 mm×2.9 mm, and an exemplary height of about 2.5 mm. When the long protective cap 410 is secured on to the sensor 400, as shown in FIG. 4, the vertical distance from the bottom of the long protective cap 410 to the bottom of the solder balls 430 is about 0.4 mm. Also, each solder pad 462 has circular column shape, with an exemplary height of about 0.1 mm, and an exemplary diameter of about 0.2 mm. Each support pad 461 has an exemplary height of about 0.38 mm. This means that there is a small gap of about 0.12 mm between bottom the long protective cap 410 and the top of the support pad 461. At these dimensions, the solder balls 430 will rest securely on the solder pads 462, and the support pads 461 will help to prevent the sensor 400 from tilting.

FIG. 3E shows an SMT process 370 (indicated by bold arrowed lines) being applied to an interface between the sensor 300A and the permanent mount 360. An example of the SMT process is reflow, which couples the solder balls 430 with the solder pads 462 to establish electrical connection. It is appreciated that the SMT process 370 often causes ambient air to include smoke, chemicals and particulars; such contaminated air may contaminate the top of the sensor 300A or 400, and adversely affect its (optical) performance.

In FIG. 4, the internal rib 415 of the second cover member (long protective cap) 410 forms an air-tight contact seal with the image sensor 400, thereby preventing the contaminated air from reaching the top of the sensor 400. In an embodiment, the air-tight contact seal is formed between the internal rib 415 and the uncoated top portion 405 of the sensor 400. It is appreciated that such a contact seal is more air-tight than the situation when the internal rib 415 contacts the coated portion 450 of the sensor 400. This is partly due to the fact that coating the sensor 400 with a coating agent will likely cause the coated surface 450 of the sensor 400 to be less smooth and/or more uneven, thereby diminishing the effectiveness of the contact seal. In general, the contact seal between the internal rib 415 and the uncoated portion 405 has a better air-tight quality.

FIG. 3F shows that after the SMT process 370 to affix the sensor 300A on to the permanent mount 360, the second cover member 310 is removed (indicated by the dotted arrow curve) from the sensor 300A. The uncoated top portion 305 of the sensor 300A is thereby exposed. It is appreciated that the top portion 305 is not contaminated by the air pollutants caused by the SMT process 370, due to the contact seal protective effect of the second cover member 310.

Embodiments of the Protective Cover Members

The first cover member 210 in FIGS. 2A through 2F, and the second cover member 310 and/or 410 in FIGS. 3A through 3F and FIG. 4 are further described herein.

Candidate material that is used to make the first cover member 210 (e.g., short protective cap) and the second cover member 310/410 (e.g., long protective member) may have specific requirements. For example, the material has high enough temperature resistance to withstand an SMT process, and also has sufficient softness to form a contact seal with the image sensor 200/300/400 without scratching or otherwise damaging it. Such a material may be a medical grade soft plastic such as silicone rubber that is stable at 250 degrees Celsius or above. Both the first cover member and the second cover member may be made by injection molding of this silicone rubber.

Figure 5A:
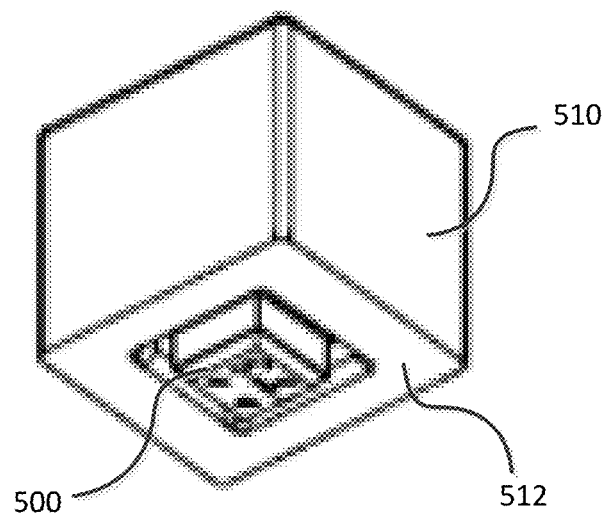
FIGS. 5A through 5H show different perspective and cross sectional views of an exemplary long protective cap.
Figure 5B:
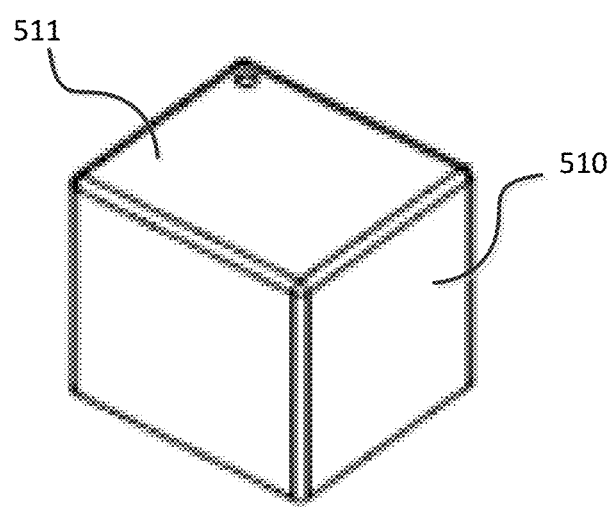
Figure 5C:
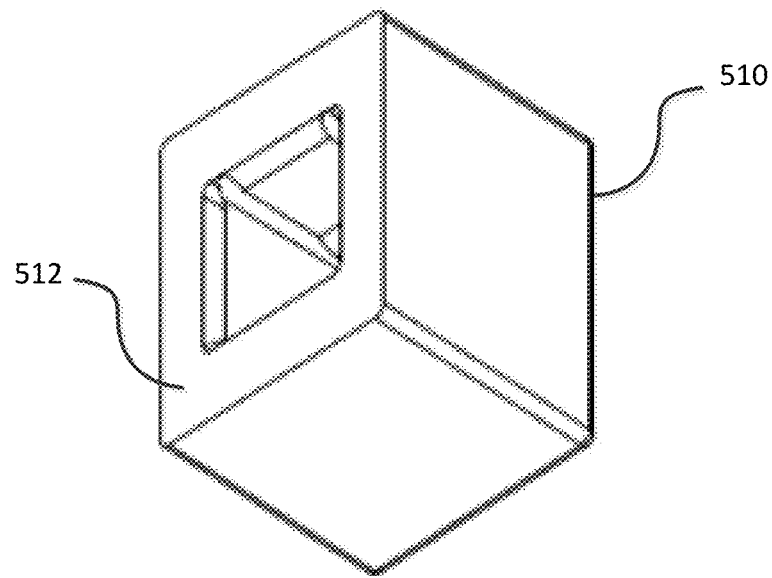

FIGS. 5A through 5H show different perspective and cross sectional views of an exemplary second cover member (long protective cap) 510. All measurements are in millimeters. FIG. 5A is a perspective bottom view that shows the second cover member 510 that covers an image sensor 500. A bottom surface 512 of the second cover member 510 is also shown. FIG. 5B is a perspective top view that shows the second cover member 510, with its top surface 511 also shown. FIG. 5C is another perspective bottom view of the second cover member 510. There is no image sensor 500 in FIG. 5C. The bottom surface 512 is also shown in FIG. 5C.

Figure 5D:
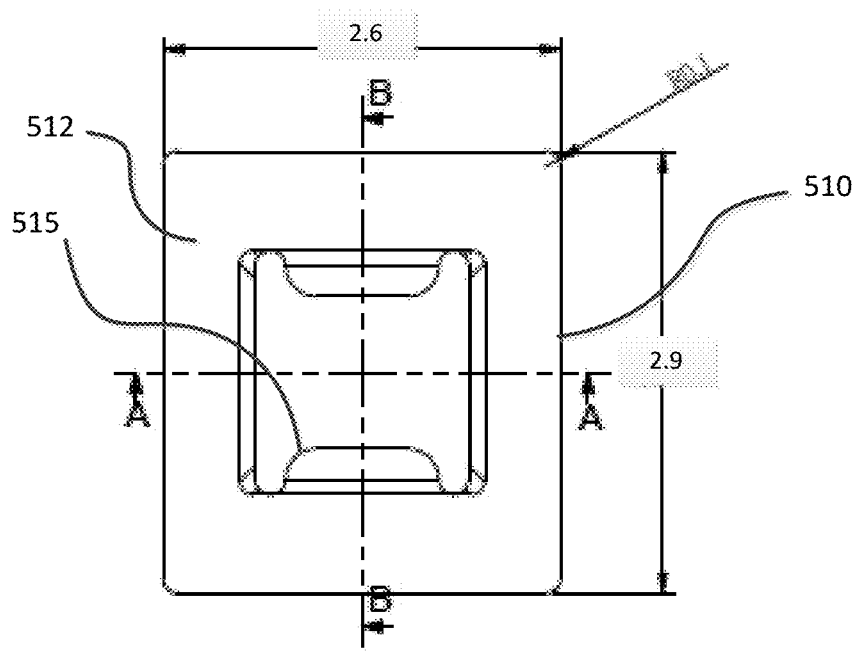

FIG. 5D is a cross sectional bottom view of the second cover member 510, showing its bottom surface 512 and a pair of internal ribs 515. This pair of internal ribs 515 may be made of silicone rubber, and may be soft enough to form a contact seal with the image sensor 500 when the second cover member 510 is placed on top of it, as exemplified in FIG. 4. The second cover member 510 has a exemplary width dimension of 2.6×2.9 mm.

Figure 5E:
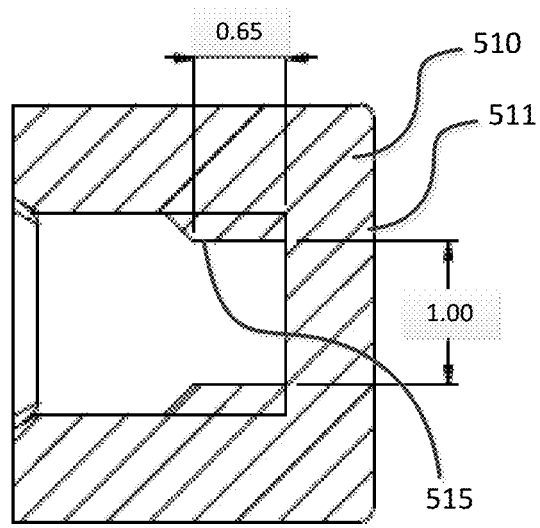
Figure 5F:
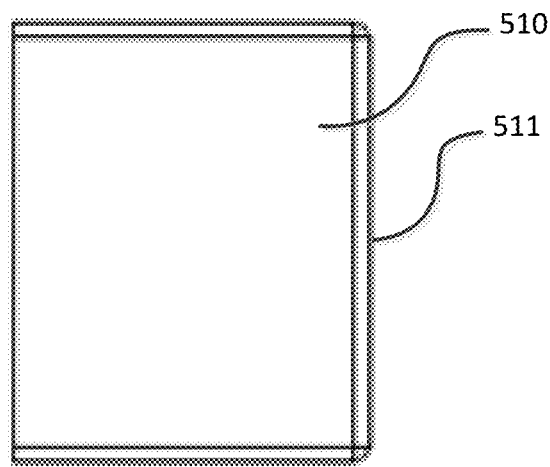

FIG. 5E is a cross sectional side view of the second cover member 510 (resting on its side surface), showing its top surface 511, and the pair of internal ribs 515. The pair of internal ribs 515 have an exemplary distance of 1 mm between them. Each internal rib 515 has a trapezoidal cross section, with exemplary parallel base sides of 0.65 mm (labeled in FIG. 5E) and 0.85 mm (not labeled in FIG. 5E). FIG. 5F is a side view of the second cover member 510 (resting on its side surface), showing its top surface 511, but the internals ribs 515 are hidden from direct view.

Figure 5G:
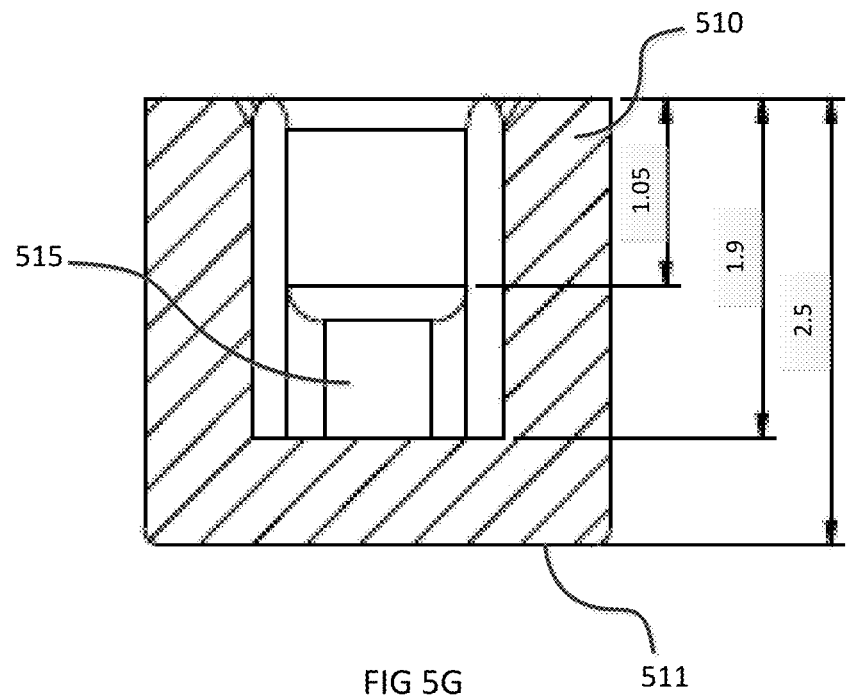
Figure 5H:
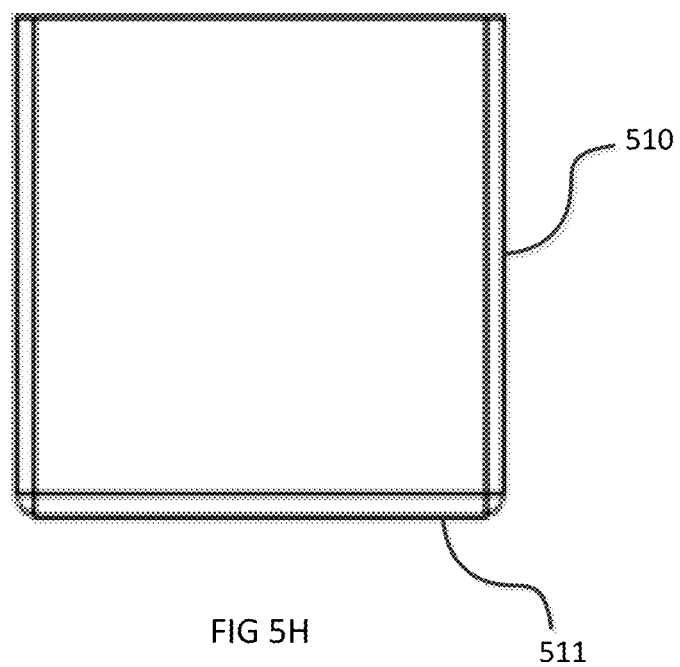

FIG. 5G is another cross sectional side view of the second cover member 510 (resting on its top surface), showing its top surface 511, as well as the internal rib 515 that is viewed at its top. At this viewing perspective, the second cover member 510 has an exemplary vertical height of 2.5 mm. Its internal cavity has an exemplary overall height of 1.9 mm. The internal cavity height that excludes the internal rib 515 is 1.05 mm. FIG. 5G is a side view of the second cover member 510 (resting on its top surface), showing its top surface 511, but the internal rib 515 is hidden from direct view.

Figure 6:
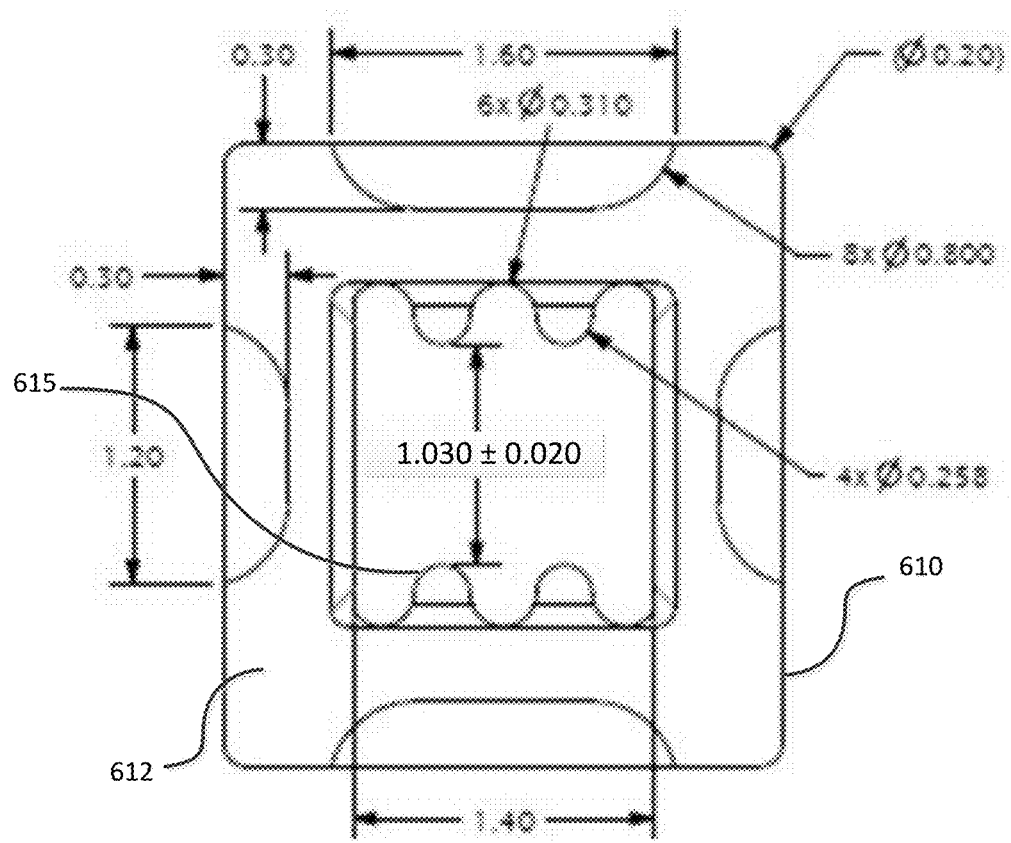
FIG. 6 is a bottom view of an alternative exemplary long protective cap.

FIG. 6 is a cross sectional bottom view of an alternative exemplary second cover member 610, showing its bottom surface 612. This figure is analogous to FIG. 5D, which shows the second cover member 510 with its pair of internal ribs 515. In FIG. 6, the alternative exemplary second cover member 610 also has its internal ribs 615. There are four of these internal ribs 615; two are located at one internal side of the second cover member 610, and the other two are located at the other internal side. Each exemplary individual internal rib 615 is a hemisphere with a diameter of 0.258 mm. The gap between an opposite pair of the internal ribs 615 is about 1.030±0.020 mm, as shown in FIG. 6. The internal ribs 615 are made of silicone rubber that is soft enough to form an air-tight contact seal with an image sensor when the second cover member 610 is placed on to the image sensor, as exemplified in FIG. 4. Other dimensions of this second cover member 610 are shown in FIG. 6. For example, the internal cavity of the second cover member 610 has a width of 1.40 mm, notwithstanding the consideration of the internal ribs 615.

Fourth Exemplary Process to Package a Small Image Sensor

Figure 9A:
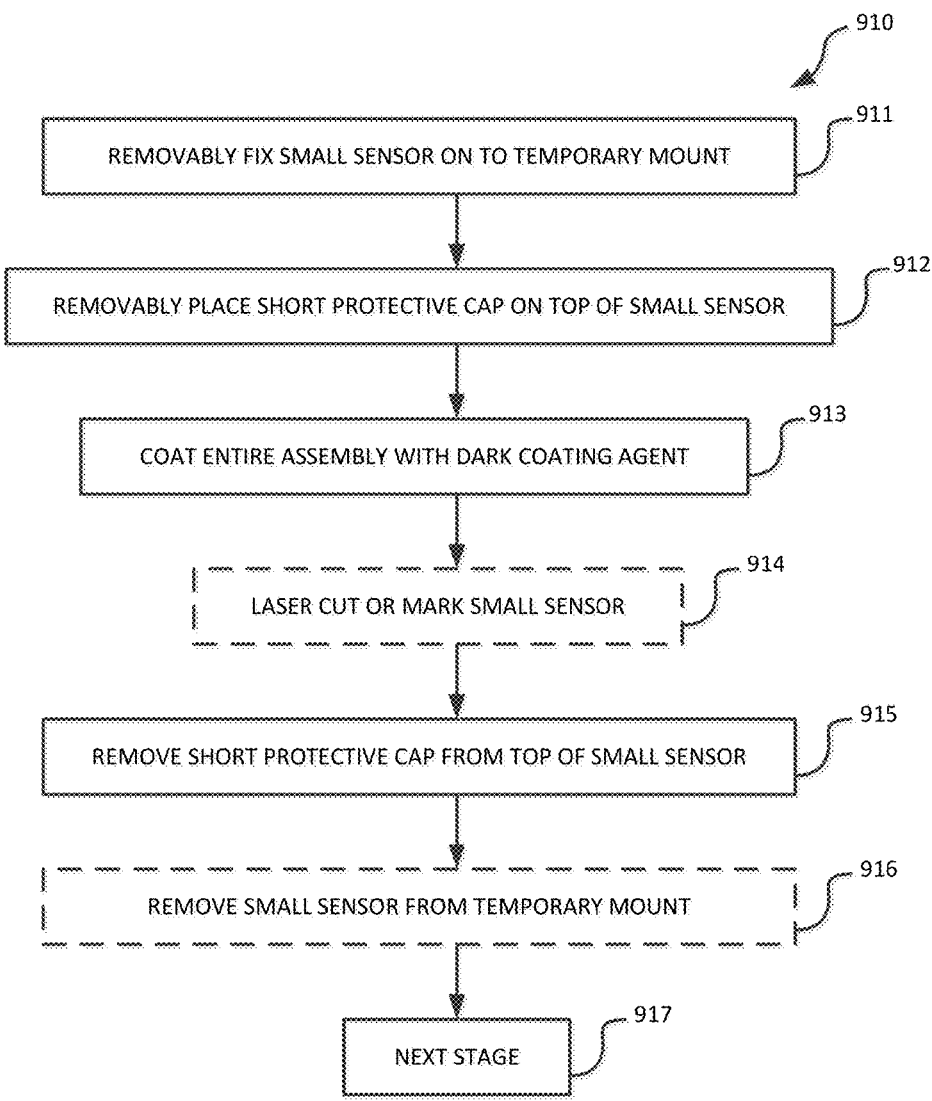
FIGS. 9A and 9B are flow charts, showing a small image sensor coating process with the use of a short protective cap, and a small image sensor mounting process with the use of a long protective cap, respectively.
Figure 9B:
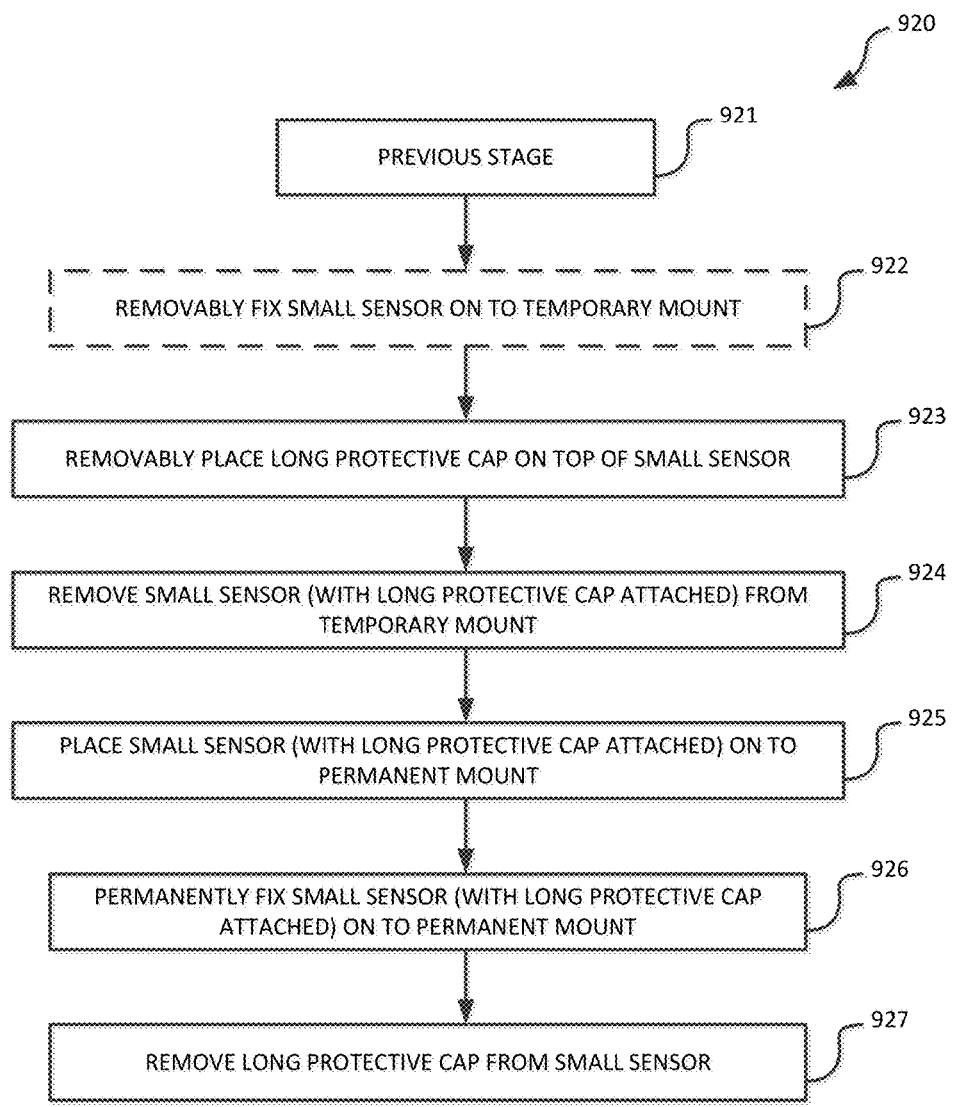

FIGS. 9A and 9B are flow charts that disclose an overall process that includes two sequential sub-processes. A first sub-process 910 coats a small image sensor with the use of a short protective cap (a first cover member), a process that has been disclosed in part earlier in FIGS. 2A through 2F. A second sub-process 920 mounts the small image sensor on to a permanent mount with the use of a long protective cap (a second cover member), a process that has been disclosed in part in FIGS. 3A through 3F, along with FIG. 4.

In FIG. 9A, the first sub-process 910 includes a step 911 to removably fix a small image sensor on to a temporary mount. This is similar to FIG. 2A, wherein the small image sensor 200 is removably fixed to the temporary mount 250 by means of a (heat activated) glue agent. Then, a step 912 removably places the first cover member 210 (short protective cap) on top of the small sensor 200, as exemplified in FIG. 2B. Next, step 913 coats the resulting cover-sensor-mount assembly with the dark coating agent 260, as exemplified in FIG. 2C. Afterwards, an optional step 914 applies the laser cutting and/or marking process 270 to the dark-coated small sensor 210A, as disclosed in FIG. 2D. Then, step 915 removes the coated first cover member 210A from the coated small sensor 200A, as exemplified in FIG. 2E. Finally, an optional step 916 removes the (coated) small sensor 200A from the (coated) temporary mount 250A to reach a next stage 917 (the last step of the sub-process 910), as exemplified in FIG. 2F.

In FIG. 9B, the second sub-process 920 starts with a previous stage step 921, which is the same as the last step of the sub-process 910 that immediately precedes the second sub-process 920. In the present embodiment, the step 921 is the same as the step 917 from the first sub-process 910. Next, an optional step 922 removably fixes a small image sensor on to a temporary mount. This is similar to FIG. 3A, wherein the small image sensor 300A is removably fixed to the temporary mount 350 by means of a (heat activated) glue agent. Then, step 923 removably places the second cover member 310 (long protective cap) on top of the small sensor 300A, as exemplified in FIG. 3B. Afterwards, a step 924 removes the small sensor 300A (with the long protective cap 310 attached to it) from the temporary mount 350, as exemplified in FIG. 3C. Next, a step 925 places the small sensor 300A (with the long protective cap 310 still attached to it) on to the permanent mount 360, as exemplified in FIG. 3D. Afterwards, a step 926 affixes the small sensor 300A (with the long protective cap 310 still attached to it) on to the permanent mount 360, as exemplified in FIG. 3E. As previously disclosed, the affixation of the small sensor 300A on to the permanent mount 360 may employ SMT techniques, such as soldering the solder balls 430 to the solder pads 462, as shown in FIG. 4. The second cover member 310 (long protective cap) may form a contact seal with the small sensor 300A (e.g., forming a contact seal with the uncoated portion 305 of the sensor 300A), and prevents the contaminated air that is generated by the SMT process from contaminating the top of the sensor 300A, as previously disclosed. Lastly, a step 927 removes the second cover member 310 (long protective cap) from the small sensor 300A, which may then be processed further to be incorporated into an image sensor system (e.g., a catheter based endoscope package) for practical application (e.g., medical endoscopy).

Fifth Exemplary Process to Package a Small Image Sensor

Figure 11:
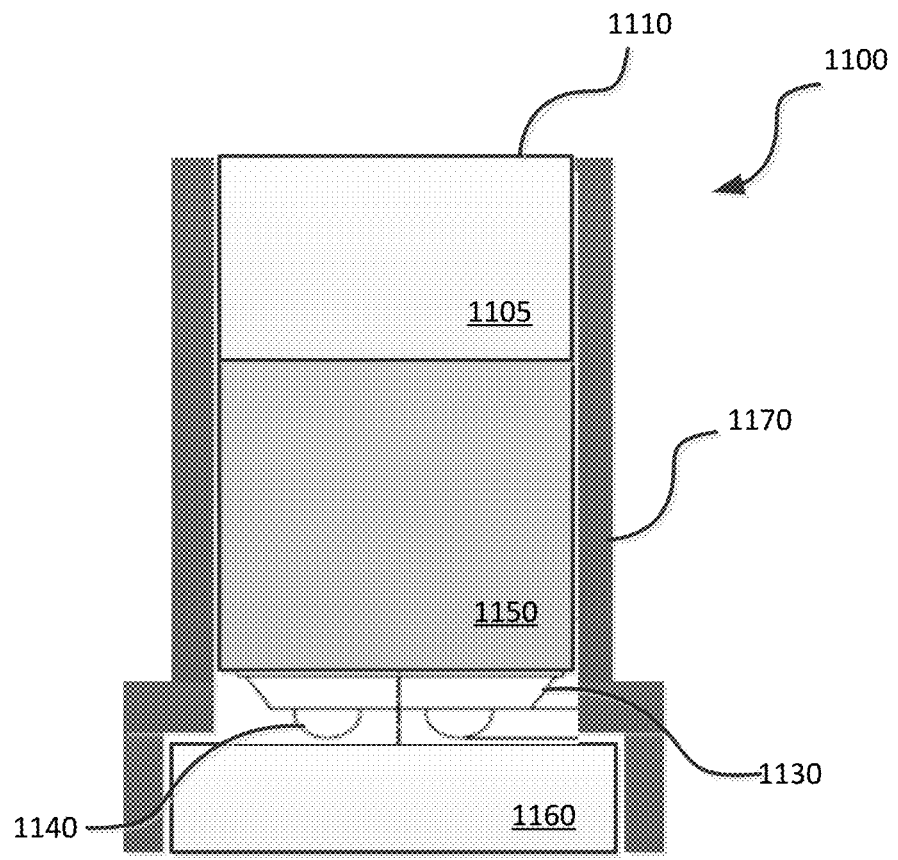
FIG. 11 is a cross sectional side view of a coated small image sensor that is mounted on a permanent mount, and is packaged with a side wall sheath.

FIG. 11 is a cross sectional side view of a packaged image sensor system 1100. The packaged image sensor system 1100 may be further incorporated into a product such as a catheter based medical endoscope. The packaged sensor system 1100 includes a coated small image sensor 1110 that is mounted on to a permanent mount 1160. The coated small image sensor 1110 is exemplified by the sensors 300A, 400, and 800B in FIG. 3F, FIG. 4, and FIG. 8B, respectively. The sensor 1110 includes a top uncoated portion 1105, and a bottom portion 1150 that is coated with a dark coating agent. These two portions make up a lens barrel component and a cover glass component of the sensor 1110. The sensor 1110 also has a silicon structure 1130 that includes image sensing elements such as photodiodes, color filters, and microlenses; as well as a number of solder balls 1140 that are coupled to the permanent mount 1160 to establish electrical connections. The silicon structure 1130 and/or the solder balls 1140 may or may not be optionally coated with the dark coating agent. In FIG. 11, they are not coated. The sensor 1110 (and optionally the permanent mount 1160) is packaged with a side wall sheath 1170 (e.g., a black light shield diaphragm), which covers up at least the uncoated portion 1105 of the sensor 1110. This covering by the sheath 1170 functions in part to prevent light from leaking out of the uncoated portion 1105. The sheath 1170 may optionally cover the coated portion 1150, and further cover the permanent mount 1160, as exemplified in FIG. 11. The additional covering by the sheath 1170 may make the packaging of the sensor 1110 easier to perform.

The above description of illustrated examples of the invention, including what is described in the Abstract, is not intended to be exhaustive or to limit the invention to the precise forms disclosed. While specific examples of the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific examples disclosed in the specification. Rather, the scope of the invention is to be determined entirely by the following claims, which are to be construed in accordance with established doctrines of claim interpretation.

What is claimed is:

1. A method of processing an image sensor system, comprising steps of:
   (a) placing a first cover member on top of an image sensor;
   (b) coating the image sensor and the first cover member with a dark coating agent;
   (c) removing the first cover member from the image sensor;
   (d) placing a second cover member on top of the image sensor;
   (e) affixing the image sensor on to a permanent mount to form an electrical coupling between the image sensor and the permanent mount;
   (f) removing the second cover member from the image sensor;
wherein the first cover member completely covers a top portion of the image sensor; and
wherein the second cover member includes an internal rib configured to form a contact seal with the image sensor.

2. The method of claim 1, further comprising a step of affixing the image sensor on to a first temporary mount, before step (a).

3. The method of claim 2, further comprising a step of cutting and marking the image sensor, between step (b) and step (c).

4. The method of claim 2, further comprising a step of removing the image sensor from the first temporary mount, between step (c) and step (d).

5. The method of claim 4, further comprising a step of affixing the image sensor on to a second temporary mount, immediately after the step of removing the image sensor from the first temporary mount, and before step (d).

6. The method of claim 5, further comprising a step of removing the image sensor from the second temporary mount, between step (d) and step (e).

7. The method of claim 1, further comprising a step of placing a sheath over the image sensor, after step (e).

8. The method of claim 1, wherein after step (b), the small image sensor includes a first portion that is not coated with the dark coating agent, and a second portion that is coated with the dark coating agent.

9. The method of claim 8, wherein the internal rib of the second cover member forms a contact seal only with the first portion of the image sensor.

10. The method of claim 1, wherein the permanent mount includes at least one solder pad, and the image sensor includes at least one solder ball; and wherein the at least one solder pad is electrically connected to the at least one solder ball.

11. The method of claim 1, wherein the image sensor has a width that is less than or equal to about one millimeter.

12. An image sensor system, comprising:
   an image sensor comprising a lens structure, a silicon structure, and solder members;
   a permanent mount that is electrically coupled to the solder members;
   wherein the lens structure includes an uncoated top portion and a bottom portion that is coated with a dark coating agent
   wherein the silicon structure is configured to convert photons to charge carriers, and to produce image signals; and
   a sheath that covers at least the uncoated top portion.

13. The image sensor system of claim 12, wherein the image sensor has a width that is less than or equal to about one millimeter.

14. A method of processing an image sensor system, comprising steps of:
   (a) placing a cover member on top of an image sensor, wherein the image sensor includes a first portion that is not coated with the dark coating agent, and a second portion that is coated with the dark coating agent;
   (b) affixing the image sensor on to a permanent mount to form an electrical coupling between the image sensor and the permanent mount;
   (c) removing the second cover member from the image sensor;
wherein the cover member includes an internal rib configured to form a contact seal with the image sensor.

15. The method of claim 14, wherein the internal rib of the cover member forms a contact seal only with the first portion of the image sensor.

16. The method of claim 14, further comprising a step of placing a sheath over the image sensor, after step (c).

17. The method of claim 14, wherein the image sensor has a width that is less than or equal to about one millimeter.

18. The method of claim 14, wherein the permanent mount includes at least one solder pad, and the image sensor includes at least one solder ball; and wherein the at least one solder pad is electrically connected to the at least one solder ball.

* * * * *